(12) United States Patent
Golden

(10) Patent No.: US 6,910,890 B2
(45) Date of Patent: Jun. 28, 2005

(54) DENTAL PLIER DESIGN WITH OFFSETTING JAW AND PAD ELEMENTS FOR ASSISTING IN REMOVING UPPER AND LOWER TEETH UTILIZING THE DENTAL PLIER DESIGN

(76) Inventor: Richard Golden, 15530 Windmill Pointe, Grosse Pointe, MI (US) 48230

( * ) Notice: Subject to any disclaimer, the term of this patent is extended or adjusted under 35 U.S.C. 154(b) by 117 days.

(21) Appl. No.: 10/306,115

(22) Filed: Nov. 27, 2002

(65) Prior Publication Data

US 2004/0101805 A1 May 27, 2004

(51) Int. Cl.[7] ............................................. A61C 3/14
(52) U.S. Cl. ............................ 433/159; 433/4; 433/215
(58) Field of Search ............................ 433/159, 4, 215

(56) References Cited

U.S. PATENT DOCUMENTS

| | | |
|---|---|---|
| 8,351 A | 9/1851 | Burch |
| 145,058 A | 12/1873 | French |
| 354,863 A | 12/1886 | Hughes |
| 908,056 A | 12/1908 | Whitney et al. |
| 1,628,499 A | 5/1927 | Joesch |
| 2,563,920 A | 8/1951 | Christensen ................ 32/62 |
| 3,866,324 A | 2/1975 | Walser ...................... 32/66 |
| 5,044,954 A | 9/1991 | Lukase et al. ............. 433/159 |
| 5,057,016 A | 10/1991 | Lukase et al. ............. 433/160 |
| 5,833,460 A | 11/1998 | Maeda ..................... 433/159 |
| 5,996,450 A | * 12/1999 | St. John ..................... 81/416 |
| 6,280,184 B1 | 8/2001 | Hamilton ................... 433/159 |
| 6,293,790 B1 | 9/2001 | Hilliard .................... 433/159 |

* cited by examiner

Primary Examiner—Cary E. O'Connor
Assistant Examiner—Candice C. Stokes
(74) Attorney, Agent, or Firm—Gifford, Krass, Groh, Sprinkle, Anderson, & Citkowski, P.C.

(57) ABSTRACT

A dental pliers appliance and associated method for removing teeth from a patient's gum line and bone. First and second pivotally connected handles are provided, each including a user grasping portion. The first handle terminates in an arcuately extending jaw exhibiting a substantially pointed end, the second handle terminates in an opposing and offset support exhibiting a support surface with an ergonomic configuration substantially matching that of the patient's gum line. Upon aligning the support along a selected location below the gum line, and further aligning the jaw in abutting fashion against an inwardly facing side of a tooth, the offset support defining a center point of rotation proximate to an edge location of the gum line and bone. The handles are subsequently rotated in an outward fashion away from the patient's gum line to forcibly dislodge the tooth from the patient's gum line and bone.

8 Claims, 5 Drawing Sheets

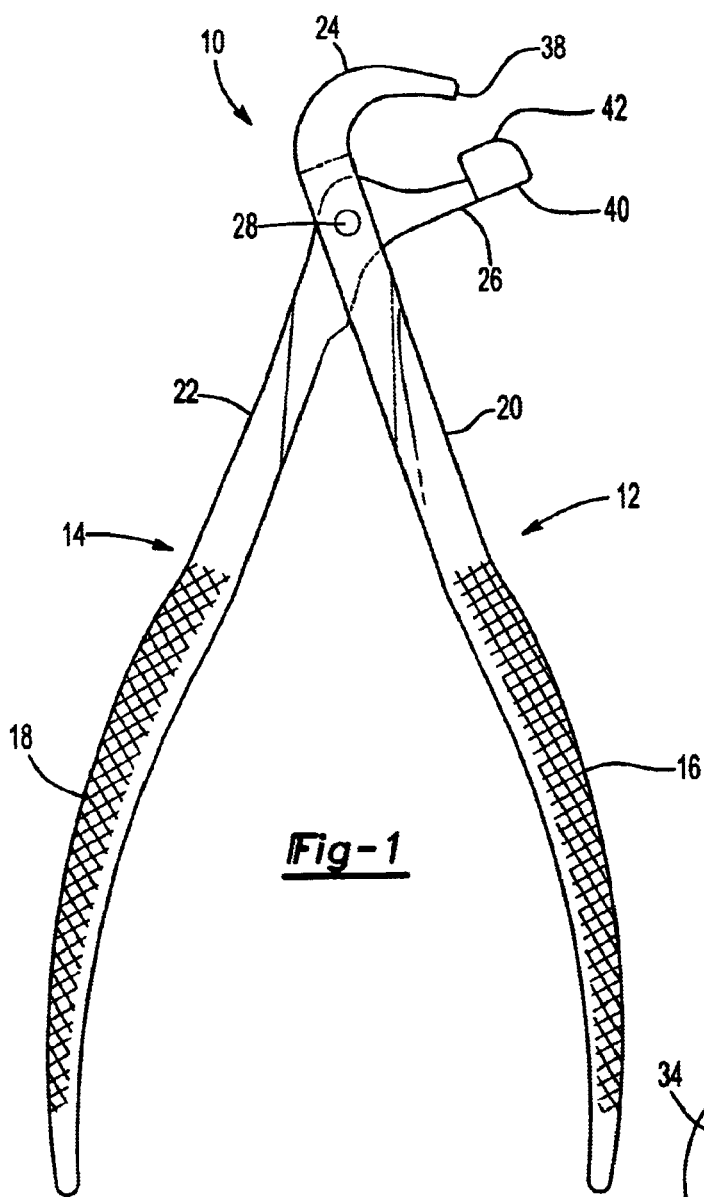
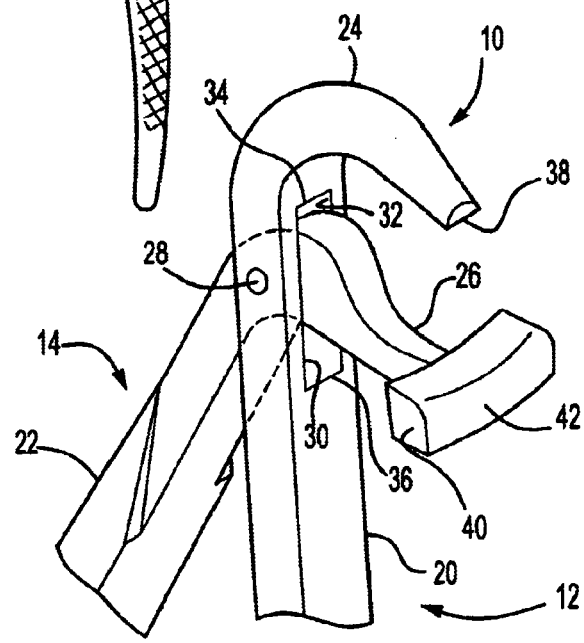
Fig-1
Fig-2

US 6,910,890 B2

DENTAL PLIER DESIGN WITH OFFSETTING JAW AND PAD ELEMENTS FOR ASSISTING IN REMOVING UPPER AND LOWER TEETH UTILIZING THE DENTAL PLIER DESIGN

BACKGROUND OF THE INVENTION

1. Field of the Invention

The present invention relates generally to dental pliers or dental forcep designs. More particularly, the present invention discloses a dental pliers design and associated method for removing teeth and which incorporates a first jaw portion and a second and offsetting handle portion, the advantage of which is to permit a two force component rotation rather than a three force component pulling, force to be applied to a selected tooth and in order to more quickly and efficiently extract the tooth from the patient's mouth.

2. Description of the Prior Art

The prior art is well documented with various types and examples of dental pliers (also known as dental forcep) designs. The general purpose of such forceps or pliers designs is to extract (or pull) a decayed and damaged tooth from a patient's mouth. All existing forcep designs require a combination of three (3) forces to remove a tooth. These include first and second opposing and aligned compressing forces exerted by the first and second jaws, combined with a third pulling or withdrawing force subsequently applied by the dentists arm. In removing the tooth, it is necessary that the jaws of the forceps be placed above the gum line on an equal and counteracting hold, accounted for by the first and second holding forces.

U.S. Pat. No. 6,280,184, issued to Hamilton, teaches a method and apparatus for removing bonded dental appliances and which includes a plier-type apparatus having first and second lever arms pivotally connected for rotation relative to each other and having respectively first and second handle portions. A hook extends from the second jaw portion and a bracing platform is pivotally connected to the first jaw portion and facing the hook. In order to remove a desired appliance, the hook is engaged at the adhesive line of the appliance and the tooth, the bracing platform further being placed against the occlusal bonded surface of the appliance, and the debonding apparatus pivoted clockwise or counterclockwise.

Both U.S. Pat. No. 8,351, issued to Burch, as well as U.S. Pat. No. 354,863, issued to Hughes, teach a dental forceps instrument having a first jaw terminating in a hook and a second jaw in an opposing and similarly pivotally associated fulcrum or disk. In each instance the tip of the hook and the center point of the fulcrum or disk are aligned at a common point.

Finally, U.S. Pat. No. 1,628,499, issued to Joesch, teaches a dental appliance article including, in one variant, a rounded and pivotally secured disk to one of the pivotal jaw portions and which interengages with a jaw of similar design to those described in the above-discussed prior art references, referring in particular to the drawings in Joesch which illustrate a shank with a pointed end and concave angular recess below the point.

SUMMARY OF THE PRESENT INVENTION

The present invention discloses a dental pliers appliance, as well as an associated method, for removing teeth and which incorporates a first jaw portion and a second and offsetting handle portion. As stated previously, the advantage of the dental pliers design of the invention is to permit the user to apply a two force component rotating force, rather than a three force component pulling force, to be applied to a selected tooth and in order to more quickly and efficiently extract the tooth from the patient's mouth and in particular from the gum line and bone in an outward direction.

The present invention is further an improvement over prior art dental appliances (pliers and/or forceps) in the design of the intentional offset or misalignment of the jaw and the support (or pad). This misalignment results in a greater and more efficient rotating force (and as opposed to a conventional pulling or withdrawing force) capable of being exerted directly upon the tooth, through the incorporation of the simplified two force rotation, and in order to quickly and efficiently remove the tooth without any damage to the patient's dental bridge.

The dental pliers appliance, according to any of the preferred embodiments, includes first and second pivotally interconnected handles. Each of the handles terminates along one end in a user-grasping portion and, at opposite extending ends, in a further selected portion suitable for engaging the patient's mouth. In particular, the first handle terminates in an arcuately extending and pointed jaw, whereas the second handle terminates in an opposing and offset support. In designing and understanding the forces necessary to extract a tooth, physics is employed. In particular, it has been found that a more efficient force is derived from a pair of offsetting and rotating forces, than that which has been previously achieved through the provision of the three force component associated with prior art forceps.

More particularly, the forces in moving a T-bar are applied to moving a tooth out of its socket and which contemplates placing a forcep (or offset support as defined in the present invention) below the gum line and on the bone of the patient. With existing forceps, this would cause a severe puncture wound in the bone and soft tissue. In use, the pointed jaw portion of the pliers appliance is positioned to abut against an inwardly facing side of a selected tooth, whereas the larger sized surface of the offset cushioned counter and support aligns along the patient's gum and below the gum line. The configuration of the dental pliers appliance is further such that the offset support defines a center point of rotation proximate an edge location of the gum line. During combined outwardly and downwardly actuated rotation of the handles, the tooth is caused to pivot forwardly and forcibly dislodge from the gum line and bone through the application of the two forces and due further to the configuration and positioning of the pointed jaw portion and offsetting support.

The configuration of the handles, with associated jaw and support portions, varies between a first variant suited for removing teeth projecting from and along a lower gum line and jaw bone of a patient and a second variant likewise suited for removing teeth projecting from and along an upper gum line. The second variant further includes first and second sub-variants, these being mirror images of one another, and which are particularly suited for engaging and dislodging teeth extending along respective halves of the upper gum line.

Additional features of the dental pliers appliance include the ability of the appliance to successfully engage and dislodge broken or fractured teeth, such as which in particular exhibit very little tooth mass extending at or above the gum line and despite having an embedded root tip. Also, it is contemplated that a sanitary, and typically flexible and plasticized, cap attachment is provided and which is capable of being releasably secured over the configured support and during such positioning of the support along the patient's gum line.

A method for removing teeth from a dental patient's gum line and bone, utilizing the dental appliance of the present invention, is also disclosed and which includes the steps of positioning a first terminating support portion of a dental pliers appliance along a selection location below the gum line, as well as concurrently positioning a second terminating and jaw portion of the dental pliers appliance against an inwardly facing side of a selected tooth projecting from the gum line. As substantially described above, first and second pivotally connected handles associated with the dental pliers appliance are then rotated in an outward fashion away from the patient's gum line and to forcibly dislodge the tooth from the patient's gum line and bone.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a plan view of a first variant of the dental pliers according to a first variant for use in removing teeth located within a patient's lower jaw and according to the present invention;

FIG. 2 is an enlarged and sectional perspective view of the dental pliers tool according to FIG. 1 and which further illustrates the jaw and support according to the present invention;

DESCRIPTION OF THE PREFERRED EMBODIMENTS

Figure 3:
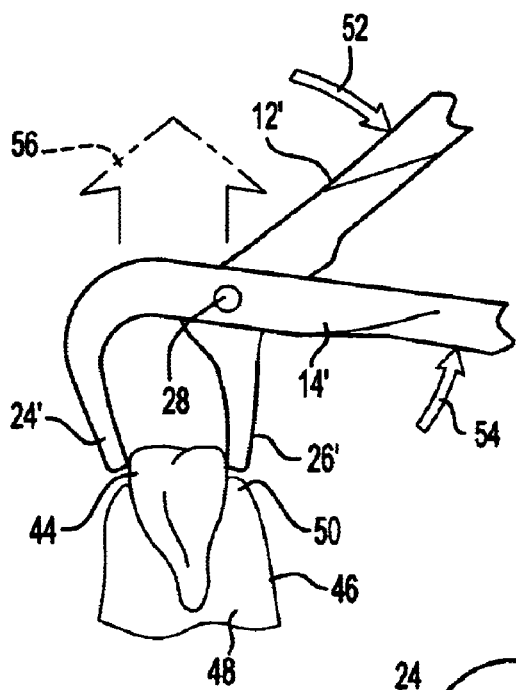
FIG. 3 is an illustration of a conventional plier design according to the prior art and further illustrating the previously known manner of withdrawing teeth utilizing a three-component pulling or withdrawing force.

Referring now to FIG. 1, a pair of dental pliers is illustrated at 10 according to a first preferred variant of the present invention and for use in removing teeth located along a lower jaw line of a patient. As discussed previously the dental pliers, according to any of the design variants disclosed herein, is an improvement over prior art dental pliers and forceps in that it facilitates providing an outward directed and rotating force, rather than a pulling force, applied to a selected tooth and in order to more quickly and efficiently extract the tooth from the patient's gum line and bone.

The present invention is again an improvement over prior art dental appliances (pliers and/or forceps) in that the intentional offset or misalignment of the jaw and the pad (or support) allows a greater and more efficient two-component rotating force (and as opposed to a conventional three-component gripping and pulling or withdrawing force) to be exerted directly upon the tooth, at the gum line, and in order to quickly and efficiently remove the tooth without any damage to the patient's dental bridge.

Referring again to FIG. 1, as well as to FIG. 2, the dental pliers variant 10 includes a first handle and a second handle, which are generally referenced at 12 and 14, respectively. Each of the handles 12 and 14 include extending and configured user grasping portions, see at 16 and 18, respectively, as well as associated intermediate portions 20 and 22 and terminating portions 24 and 26. In the particular instance of the variant of FIGS. 1 and 2, the configuration of the dental pliers appliance 10 illustrated is specifically suited for the dislodging and removal of teeth located along a lower gum line and jaw bone of a patient.

The handles 12 and 14 are further hingedly interconnected at pivot point 28. In a preferred variant, an aperture is defined along and within the first handle 12, and such as is best illustrated in FIG. 2 by inwardly facing side walls 30 and 32 and interconnecting end walls 34 and 36 which define an elongated and rectangular slot shaped aperture. The aperture in first handle 12 is located in proximity to its terminating end 24 and such that the second handle 14, a point intersecting the first handle 12, extends through the aperture. A pin (again defined by pivot point 28) extends crosswise through the intersecting location of the first and second handles 12 and 14 to define the pivotal connection. It is further understood that both the configuration of gripping portions of the handles, as well as the manner in which the handles are pivotally connected together, may be modified without departing from the scope of the invention.

Referring again to FIGS. 1 and 2, the terminating portion 24 (associated with first handle 12) exhibits an arcuately extending and substantially pointed jaw 38. In contrast, the second terminating portion 26 (associated with second handle 14) exhibits a three dimensional and offset support 40 exhibiting an ergonomically configured and supporting surface 42 which is designed to substantially match that of the patient's gum line.

Figure 4:
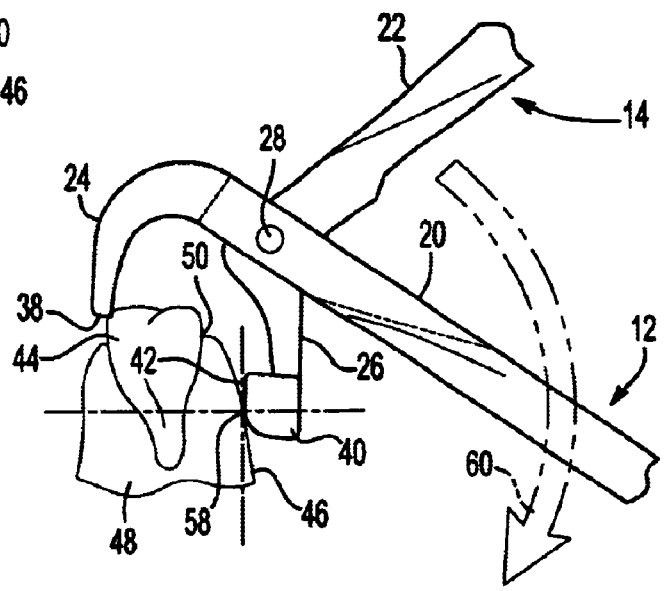
FIG. 4 is an illustration, of a nature similar to that shown in FIG. 1, and showing the tool according to FIGS. 1 and 2 in a first engaged position relative a patient's tooth located along the bottom jaw.
Figure 5:
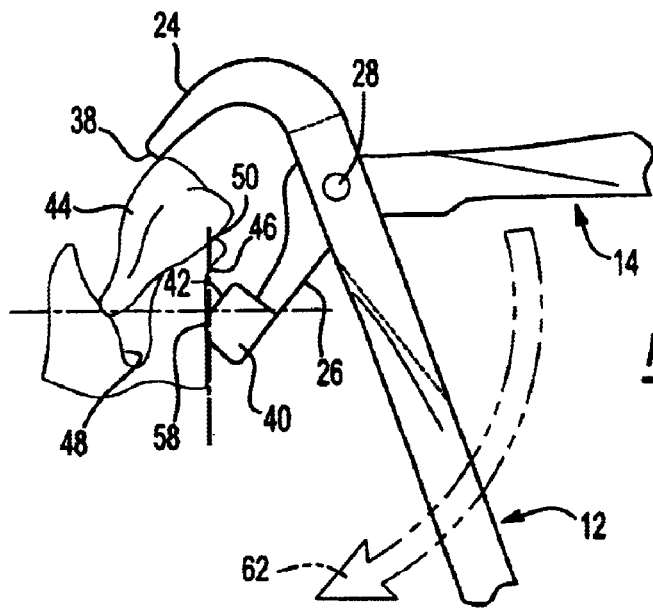
FIG. 5 is an illustration of a furthering removal or cantilevered position of the tooth and in which the tool, also shown in FIG. 4, is rotated utilizing a two-component force application and resulting in the tooth being forcibly disengaged from the patient's lower bridge and gum line.

Prior to providing a description of the engaging and removal positions of the appliance 10, relative to a patient's tooth and as is shown in FIGS. 4 and 5, a description of the prior art and existing technique for removing a tooth will now be explained and with further reference to FIG. 3. In particular, conventionally designed handles 12' and 14' are shown in the Prior Art view of FIG. 3, are pivotally connected at 28', and terminate in associated and opposing ends 24' and 26' in the form of jaw portions.

As further shown in FIG. 3, the prior art technique for removing a selected tooth 44 from its associated gum 46 and bone 48 contemplates the opposing jaw portions, see again 24' and 26', engaging opposite facing sides of the tooth 44, above a gum line 50 from which the tooth 44 projects. Upon positioning of the prior art pliers device in the position illustrated in FIG. 3, and further upon the handles 12' and 14' being compressed in the directions illustrated at 52 and 54, (accounting for the first and second forces) respectively, a further (third) pulling force (referenced by directional arrow 52) is concurrently applied in a direction opposite that of the holding force established between the tooth 44 and the patient's gum 46 and bone 48. While eventually effective in removing the patient's tooth 44, it has been found that the prior art application of FIG. 3 results in both the requirement of extensive time and effort necessary to successfully dislodge the tooth, resulting in the requirement of the three pulling forces, this having a commensurate effect on the patient's comfort level as well as increasing the likelihood of the tooth becoming fractured or broken during the removal process.

Referring again to FIGS. 4 and 5, first engagement and second actuating positions are again illustrated in reference to the dental appliance tool and method of operation according to the present invention. In particular, and referencing first FIG. 4, the said support 40, with ergonomic surface 42, is illustrated in position along a selected location of the patient's gum 46 and below the gum line 50.

Upon further aligning of the opposing and pointed jaw 38 in abutting fashion against an inwardly facing side of the tooth, again shown at 44 and above the gum line, the offset support 40 defines a center point of rotation 58 proximate an edge location of the gum line 46 and bone 48. The handles 12 and 14 are then initiated in a rotating direction in an outward fashion away from the patient's gum line 46, as illustrated by directional arrow 60, and resulting in the pair of rotating forces being applied to the tooth about the axis of rotation.

Referring further to FIG. 5, continued rotation of the handles 12 and 14 along the direction of arrow 62 causes a cantilever or dislodging force to be applied to the tooth 44, about the center point of rotation 58, and so that the tooth 44 is caused to be forcibly dislodged, along the gum line 50, and from the patient's gum 46 and associated bone 48. Of significant advantage is the ability to apply a single and multiplied rotating and cantilevering force to the dental pliers appliance (accounted for by the pair of forces), and which is measured by the offsetting distance between the edge of the jaw 38 and the center point of rotation 58 established by the support 40. The configuration of the support surface 40 is further such that it comfortably engages upon the tissue and bone during the two-component rotating force and without damaging the soft tissue and bone during the force rotation, this again not possible with prior art forcep designs. The ability to apply such a combined and unidirectional rotating force causes the tooth 44 to be much more quickly dislodged and removed than in the instances of the prior art in which grasping forces 52 and 54 (first and second forces) tend to cancel out a significant degree of the pulling/withdrawing force 56 (third force) (see again FIG. 3) and by which no effective cantilevering or rotating forces are created to assist in tooth removal.

Figure 6:
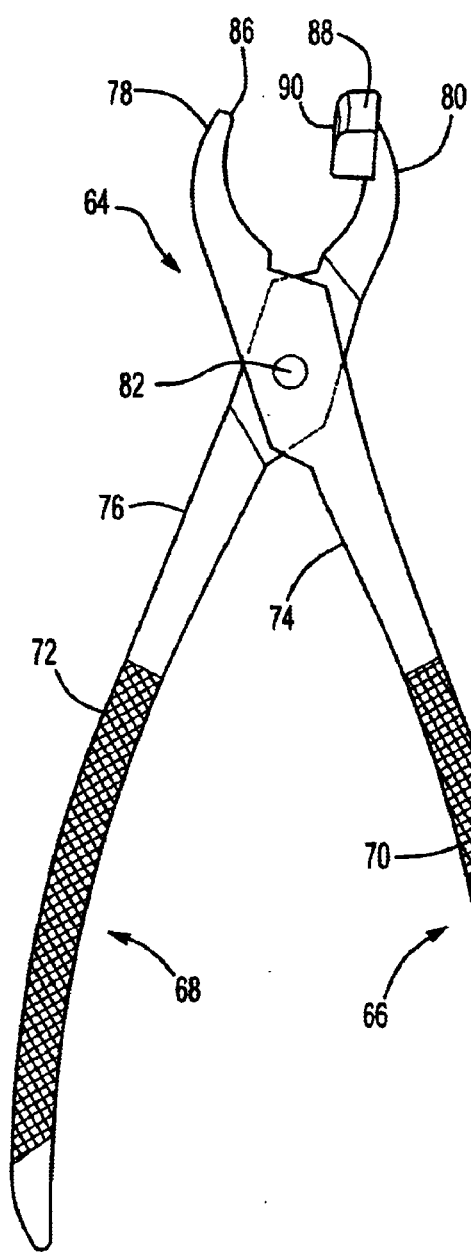
FIG. 6 is plan view of a second variant of the dental pliers tool for use in removing teeth located along a first half of a patient's upper jaw and according to the present invention.
Figure 7:
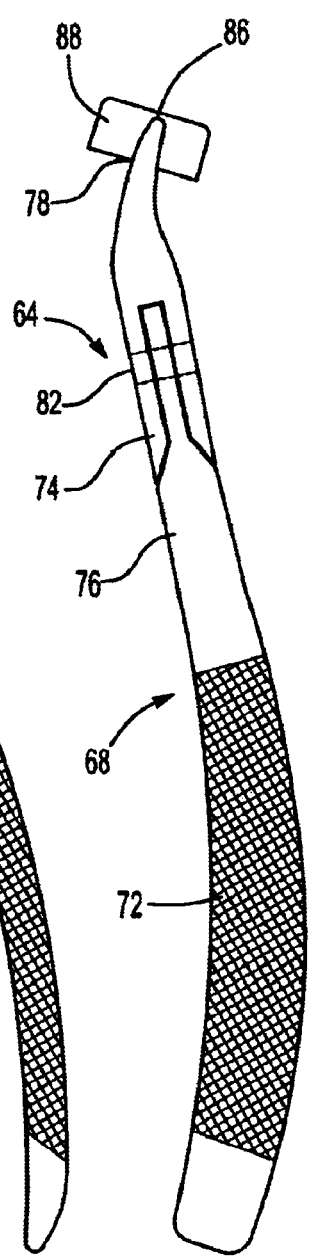
FIG. 7 is a side view of the dental pliers tool illustrated in FIG. 6 and according to the present invention.

Referring now to FIGS. 6 and 7, plan and side views are illustrated, respectively, of a second variant 64 of a dental pliers appliance for use in removing teeth according to the present invention. In particular the variant 64 of FIGS. 6 and 7, and as will be further explained in reference to FIGS. 10 and 11, is suited for removing teeth located along a patient's upper jaw and gum line.

The features of the dental pliers appliance 64 are essentially the same as those associated with the variant 10 illustrated in FIGS. 1 and 2 and again include handles 66 and 68 with grasping portions 70 and 72, intermediate extending portions 74 and 76, and configured and opposing terminating portions 78 and 80. The appliance 64 further includes a pivotal connection 82 constructed in substantially the same fashion as that described and illustrated in the first preferred and lower jaw embodiment and which again includes the provision of an aperture (see at 84 in FIG. 9) defined in the first handle 66 and through which an intersecting portion of the second handle 68 passes and which is held in place by a pin associated with the pivotal connection 82.

Figure 9:
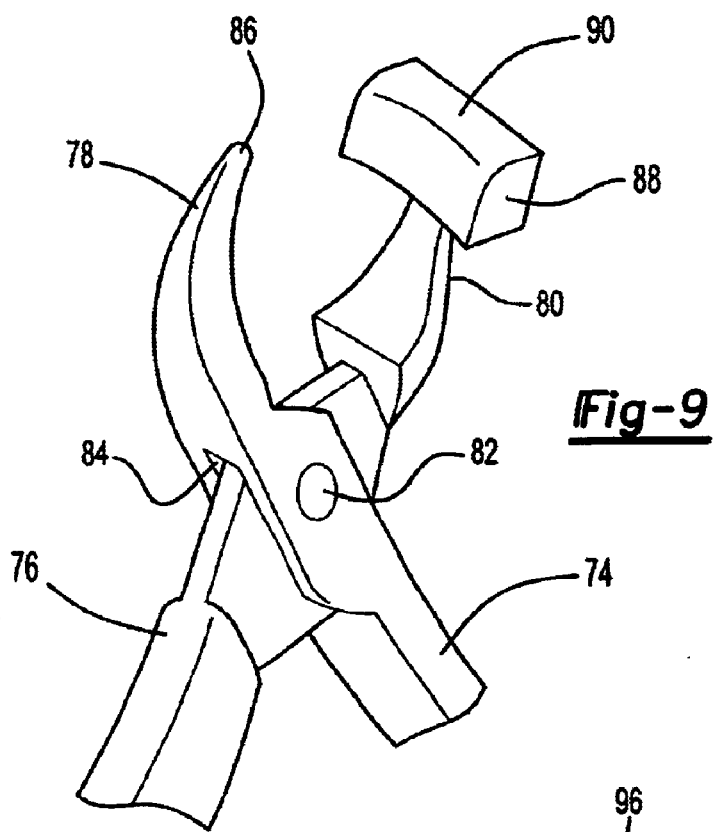
FIG. 9 is an enlarged and sectional perspective view of the dental pliers tool according to the upper jaw variant of FIG. 8 and which further illustrates the jaw and support according to the present invention.

As also shown in FIG. 9, the terminating portion 78 is again provided with a pointed and angled jaw 86 and the terminating portion 80 as a support 88 with ergonomically configured surface 90. Referring further to FIGS. 10 and 11, engagement and removal positions are illustrated of the appliance 64 in relation to a tooth 92 located within an upper gum 94 and bone 96 of a patient.

Figure 10:
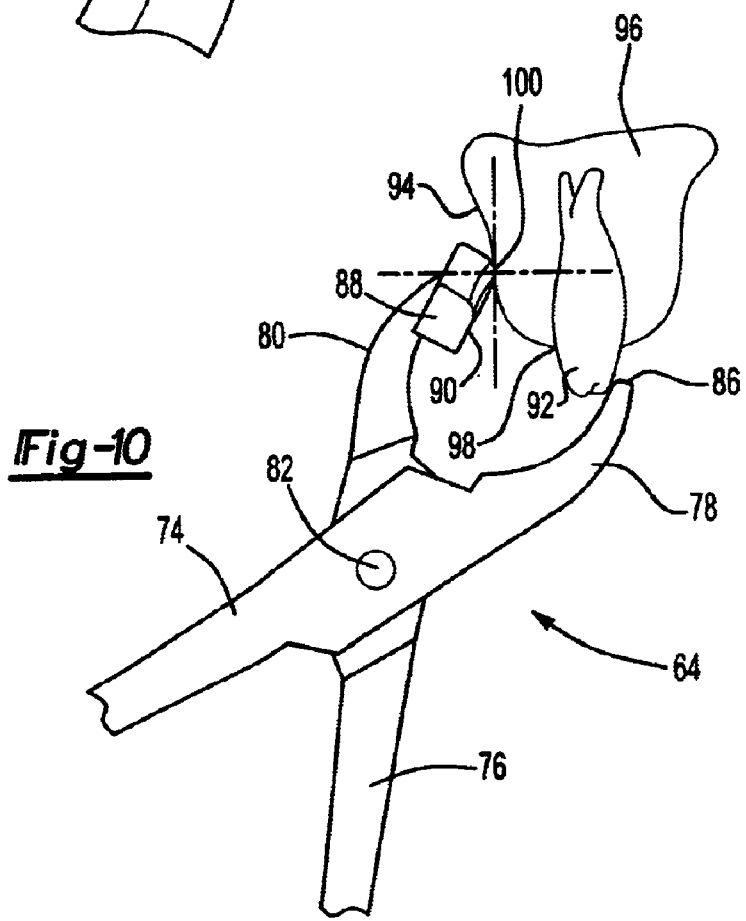
FIG. 10 is an illustration, of a nature similar to that previously shown in FIG. 4, and showing the tool according to either of the sub-variants of FIGS. 7 and 8, in a first engaged position relative a patient's tooth located along a selected half of the upper jaw.
Figure 11:
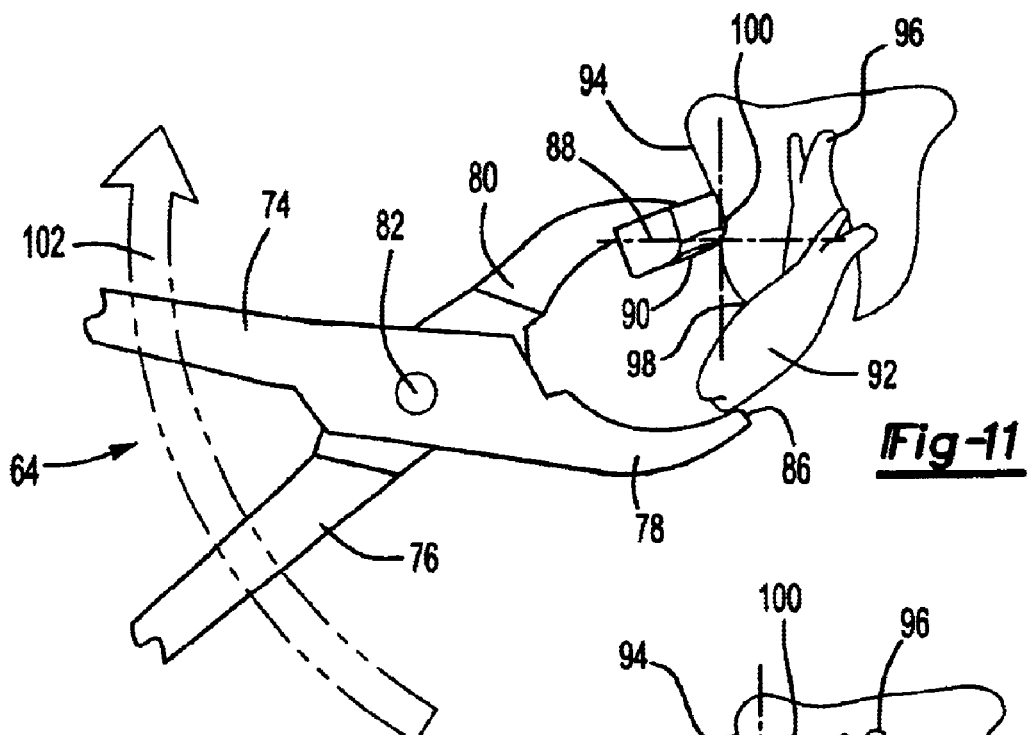
FIG. 11 is an illustration of a furthering removal or cantilevered position of the tooth and in which the tool, also shown in FIG. 10, is rotated resulting in the tooth again being forcibly disengaged from the patient's upper bridge and gum line through a two-component rotating force according to the present invention.

As illustrated in the initial engagement position of FIG. 10, the support 88 with ergonomic surface 90 is positioned against the gum 94, at a position above in this instance the patient's upper jaw gum line 98. At the same time, the angled jaw 86 is again abutted against an inwardly facing side of the tooth 92 and in order to define a center point of rotation 100 of the support 88 which is offset the desired distance from the jaw 86 and the upper gum line 98.

Referring further to FIG. 11, a rotating and cantilevering force (two-component force) is applied along the handles of the appliance 64, in the direction of arrow 102, and so that the selected upper tooth 92 is likewise rotated and forcibly dislodged from the gum 94 and bone 96 defining the patient's upper bridge. The same forces of physics apply in the upper jaw variant 64 of the appliance, as compared to those illustrated and described in reference to the lower jaw appliance 10 in FIGS. 4 and 5, and by which the rotating and cantilevering forces about the center point of rotation effectively and efficiently actuate, dislodge and remove the tooth in the desired pivoting fashion about the gum line with a minimum of time and effort and without damage to the patient's soft tissue and bone.

Figure 8:
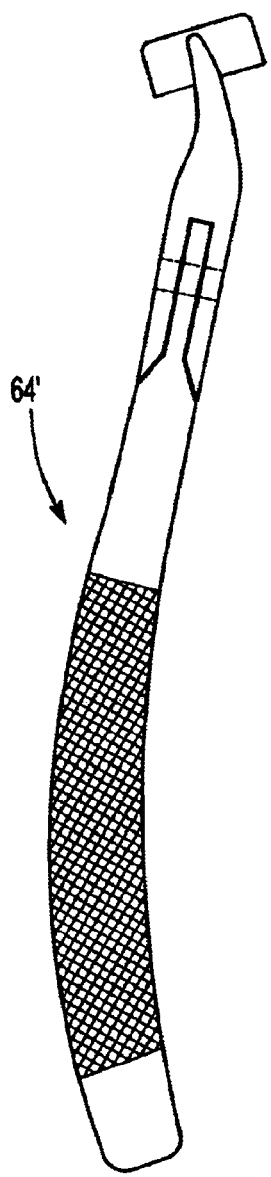
FIG. 8 is a side view of an opposite and mirror image dental pliers tool, with respect to that illustrated in FIGS. 6 and 7, and which is used for removing teeth located along a second half of a patient's upper jaw.

Referring to FIG. 8, a side view of an opposite and mirror image dental pliers tool, see at 64', is illustrated and with respect to that illustrated at 64 in FIGS. 6 and 7. In particular, the tool 64' is an identically constructed, albeit again mirrored image configuration, of the variant 64 and for the specific purpose of removing teeth located along a selected and second half of a patient's upper jaw. In comparison, the variant 64 is suited for removing teeth from a first upper extending half of the patient's jaw and the particular ergonomic configuration of either of the appliance variants 64 or 64', when viewed in side profile, is depending upon that which is easiest to grasp and manipulate during the engaging and dislodging procedure. The mirrored image sub-variant 64' is otherwise identically constructed as that illustrated at 64 such that a repetitive description of its elements is not required.

Figure 12:
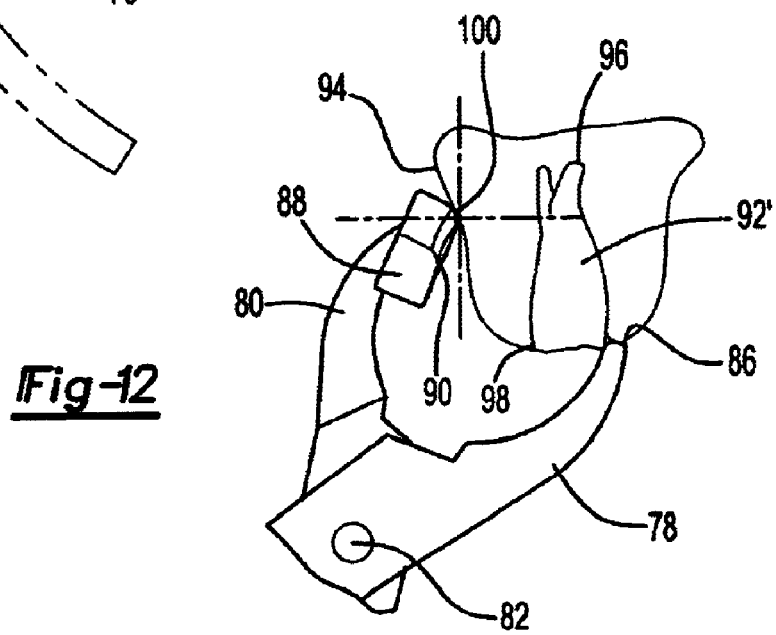
FIG. 12 is a view similar to that previously shown in FIG. 10 and in which the dental pliers design is illustrated in a further engagement position for forcibly removing a broken or fragmented tooth having an embedded root tip.

Referring to FIG. 12, a view similar to that previously shown in FIG. 10 is illustrated and by which the dental pliers design, such as the variant at 64, is illustrated in a further engagement position for forcibly removing a broken or fragmented tooth 92' having a likewise embedded root tip within the gum 94 and bone 96 of the patient's upper jaw. The purpose of the illustration of FIG. 12 is in illustrating that the dental appliance tool, whether of the lower jaw variant 10 or a selected upper jaw sub-variant 64 or 64', is capable of effectively engaging and removing even broken or fractured teeth in which little or not tooth mass is evident above or below the associated gum line.

Figure 13:
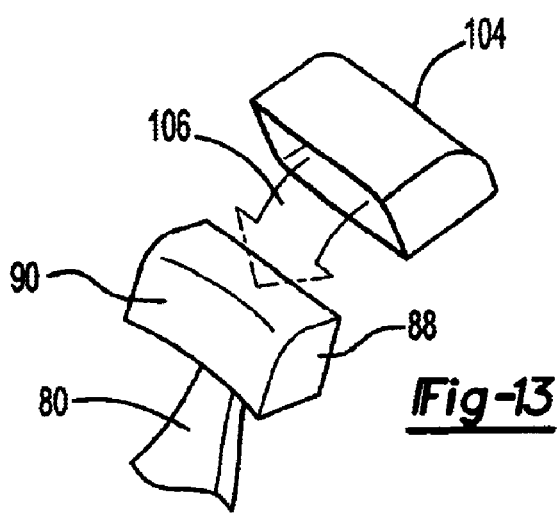
FIG. 13 is a sectional illustration of a plasticized and sterile cap attachment for use with the support according to any previously illustrated variant according to the present invention.

Referring further to FIG. 13, a sectional illustration of a plasticized and sterile cap attachment 104 is illustrated for use with the support (such as for example illustrated at 88) according to any previously illustrated variant according to the present invention. The cap attachment 104 exhibits a three dimensional body with a hollowed interior and is constructed of a plasticized and flexible material. The cap 104 is further capable of being releasably secured, in the manner illustrated by arrow 106, upon the support 88 and is further configured for mating with the ergonomic configuration (see at 90) associated with that support.

As previously described, a method for removing teeth from a dental patient's gum line and bone using the dental appliance tool of the present invention, is also disclosed and includes the steps of positioning a first terminating portion of a dental pliers appliance along a selection location below the gum line and concurrently positioning a second terminating portion of the dental pliers appliance against an inwardly facing side of a selected tooth projecting from the gum line. The first and second pivotally connected handles associated with the dental pliers appliance are then rotated in an outward fashion away from the patient's gum line applying a two-component force, to forcibly dislodge the tooth from the patient's gum line and bone.

Additional steps of the present method include offsetting the first terminating portion from the second terminating portion and such that the first portion defines a center point of rotation proximate an edge location of the gum line, as well as ergonomically configuring the first terminating portion to substantially match that of the patient's gum. Yet additional steps include configuring the second terminating portion with a substantially pointed end, as well as configuring the dental pliers appliance to engage and dislodge a tooth located along either the lower or upper gum line and associated jaw bone of a patient. Still further method steps include angling a side profile of the first and second pivotally connected handles, according to either upper jaw sub-variant of the appliance, as well as again releasably securing a plasticized and sterilized cap attachment over the ergonomically configured and first terminating portion.

Having described my invention, additional preferred embodiments will become apparent to those skilled in the art to which it pertains and without deviating from the scope of the appended claims.

I claim:

1. A method for removing teeth from a dental patient's gum line and bone, said method comprising the steps of:

positioning a first terminating portion of dental pliers appliance along a selection location below the gum line;

positioning a second terminating portion of the dental pliers appliance against an inwardly facing side of a selected tooth projecting from the gum line; and rotating first and second pivotally connected handles associated with the dental pliers appliance in an outward fashion away from the patient's gum line to forcibly dislodge the tooth from the patient's gum line and bone.

2. The method as described in claim 1, further comprising the step of offsetting the first terminating portion from the second terminating portion and such that said first portion defines a center point of rotation proximate an edge location of the gum line.

3. The method as described in claim 1, further comprising the step of ergonomically configuring the first terminating portion to substantially match that of the patient's gum.

4. The method as described in claim 1, further comprising the step of configuring the; second terminating portion with a substantially pointed end.

5. The method as described in claim 1, further comprising the step of configuring the dental pliers appliance to engage and dislodge a tooth located along a lower gum line and jaw bone of a patient.

6. The method as described in claim 1, further comprising the step of configuring the dental pliers appliance to engage and dislodge a tooth located along an upper gum line and jaw bone of a patient.

7. The method as described in claim 6, further comprising the step of angling a side profile of the first and second pivotably connected handles.

8. The method as described in claim 3, further comprising the step of releasably securing a plasticized and sterilized cap attachment over the ergonomically configured and first terminating portion.

\* \* \* \* \*